US00PP21662P2

(12) United States Plant Patent
Sakazaki

(10) Patent No.: US PP21,662 P2
(45) Date of Patent: Jan. 18, 2011

(54) ***NIEREMBERGIA* PLANT NAMED 'USNRB1201'**

(50) Latin Name: *Nierembergia hybrida*
Varietal Denomination: USNRB1201

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 12/653,193

(22) Filed: Dec. 9, 2009

(51) Int. Cl.
*A01H 5/00* (2006.01)

(52) U.S. Cl. ..... Plt./459

(58) Field of Classification Search ..... Plt./459
See application file for complete search history.

*Primary Examiner*—Annette H Para
(74) *Attorney, Agent, or Firm*—C. A. Whealy

(57) ABSTRACT

A new and distinct cultivar of *Nierembergia* plant named 'USNRB1201', characterized by its compact, upright, outwardly spreading and mounding plant habit; freely branching habit; freely and early flowering habit; large violet blue-colored flowers; relatively long flowering period; and good garden performance.

1 Drawing Sheet

Botanical designation: *Nierembergia hybrida.*
Cultivar denomination: 'USNRB1201'.

BACKGROUND OF THE INVENTION

The present invention relates to a new and distinct cultivar of *Nierembergia* plant, botanically known as *Nierembergia hybrida* and hereinafter referred to by the name 'USNRB1201'.

The new *Nierembergia* plant is a product of a planned breeding program conducted by the Inventor in Higashiomi, Shiga, Japan and Bonsall, Calif. The objective of the breeding program was to create new compact and mounding *Nierembergia* cultivars with early flowering habit and strong foliage.

The new *Nierembergia* plant originated from a cross-pollination made by the Inventor on Jun. 10, 2005 in Higashiomi, Shiga, Japan, of an unnamed selection of *Nierembergia caerulea*, not patented, as the female, or seed, parent with a proprietary selection of *Nierembergia hybrida* identified as code number UCU-1, not patented, as the male, or pollen, parent. The new *Nierembergia* plant was discovered and selected by the Inventor as a single flowering plant within the progeny of the stated cross-pollination in a controlled environment in Bonsall, Calif. on Jul. 6, 2006.

Asexual reproduction of the new *Nierembergia* plant by vegetative cuttings in a controlled environment in Bonsall, Calif. since Jul. 10, 2006, has shown that the unique features of this new *Nierembergia* plant are stable and reproduced true to type in successive generations.

SUMMARY OF THE INVENTION

Plants of the new *Nierembergia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USNRB1201'. These characteristics in combination distinguish 'USNRB1201' as a new and distinct cultivar of *Nierembergia:*

1. Compact, upright, outwardly spreading and mounding plant habit.
2. Freely branching habit.
3. Freely and early flowering habit.
4. Large violet blue-colored flowers.
5. Relatively long flowering period.
6. Good garden performance.

Plants of the new *Nierembergia* differ from plants of the female parent selection in the following characteristics:

1. Plants of the new *Nierembergia* are more freely branching than plants of the female parent selection.
2. Plants of the new *Nierembergia* flower earlier than plants of the female parent selection.
3. Plants of the new *Nierembergia* have lighter-colored flowers than plants of the female parent selection.

Plants of the new *Nierembergia* differ from plants of the male parent selection in the following characteristics:

1. Plants of the new *Nierembergia* flower for a longer period of time than plants of the male parent selection.
2. Plants of the new *Nierembergia* and the male parent selection differ in flower color as plants of the male parent selection have pale blue-colored flowers.

Plants of the new *Nierembergia* can be compared to plants of *Nierembergia hippomanica* 'Blue Eye', disclosed in U.S. Plant Pat. No. 16,314. In side-by-side comparisons conducted in Bonsall, Calif., plants of the new *Nierembergia* and 'Blue Eye' differed primarily in the following characteristics:

1. Leaves of plants of the new *Nierembergia* were not chlorotic whereas leaves of plants of 'Blue Eye were chlorotic'.
2. Plants of the new *Nierembergia* flowered earlier than plants of 'Blue Eye'.

Plants of the new *Nierembergia* can also be compared to plants of *Nierembergia* 'Mont Blanc', not patented. In side-by-side comparisons conducted in Bonsall, Calif., plants of the new *Nierembergia* and 'Mont Blanc' differed primarily in the following characteristics:

1. Plants of the new *Nierembergia* and 'Mont Blanc' differed in flower color as plants of 'Mont Blanc' had white-colored flowers.

2. Plants of the new *Nierembergia* flowered earlier than plants of 'Mont Blanc'.

BRIEF DESCRIPTION OF THE PHOTOGRAPHS

The accompanying colored photographs illustrate the overall appearance of the new *Nierembergia* plant showing the colors as true as it is reasonably possible to obtain in colored reproductions of this type. Colors in the photographs may differ slightly from the color values cited in the detailed botanical description which accurately describe the actual colors of the new *Nierembergia* plant.

The photograph at the bottom of the sheet comprises a side perspective view of a typical flowering plant of 'USNRB1201' grown in a container.

The photograph at the top of the sheet is a close-up view of typical flowers and leaves of 'USNRB1201'.

DETAILED BOTANICAL DESCRIPTION

Plants used for the aforementioned photographs and following description were grown under conditions which closely approximate commercial production conditions during the autumn in 12.5-cm containers in an outdoor nursery in Bonsall, Calif. During the production of the plants, day temperatures ranged from 18° C. to 38° C., night temperatures ranged from 9° C. to 18° C. and light levels ranged from 7,000 to 10,000 foot-candles. Plants were pinched one time and were six weeks old when the photographs and description were taken. In the following description, color references are made to The Royal Horticultural Society Colour Chart, 2007 Edition, except where general terms of ordinary dictionary significance are used.

Botanical classification: *Nierembergia hybrida* 'USNRB1201'.

Parentage:

*Female, or seed, parent.*—Unnamed selection of *Nierembergia caerulea*, not patented.

*Male, or pollen, parent.*—Proprietary selection of *Nierembergia hybrida* identified as code number UCU-1, not patented.

Propagation:

*Type cutting.*—Vegetative tip cuttings.

*Time to initiate roots, summer.*—About four days at temperatures ranging from 17° C. to 29° C.

*Time to initiate roots, winter.*—About six days at temperatures ranging from 17° C. to 21° C.

*Time to produce a rooted plant, summer.*—About 22 days at temperatures ranging from 17° C. to 29° C.

*Time to produce a rooted plant, winter.*—About 25 days at temperatures ranging from 17° C. to 21° C.

*Root description.*—Medium in thickness; white in color.

*Rooting habit.*—Freely branching; dense.

Plant description:

*Plant form/habit.*—Compact, upright, outwardly spreading and mounding plant habit; vigorous growth habit; freely branching habit with about eight primary lateral branches each with multiple secondary and tertiary lateral branches; pinching enhances branching potential.

*Plant height.*—About 11 cm.

*Plant width (spread).*—About 35 cm.

*Lateral branches.*—Length: About 19 cm. Diameter: About 2 mm. Internode length: About 8 mm. Strength: Strong; wiry. Texture: Pubescent. Color: Close to 138A.

Foliage description:

*Arrangement.*—Alternate, simple; sessile.

*Length.*—About 2.4 cm.

*Width.*—About 2.5 mm.

*Shape.*—Lanceolate.

*Apex.*—Acute.

*Base.*—Attenuate.

*Margin.*—Entire.

*Texture, upper and lower surfaces.*—Smooth, glabrous.

*Venation pattern.*—Pinnate.

*Color.*—Developing leaves, upper surface: Close to 146A. Developing leaves, lower surface: Close to 146B. Fully expanded leaves, upper and lower surfaces: Close to 146B; venation, close to 146B.

Flower description::

*Flower type/habit.*—Single actinomorphic funnelform flowers; flowers face mostly upright to outwardly; freely flowering habit with about 37 to 42 flowers and flower buds per lateral stem.

*Fragrance.*—None detected.

*Natural flowering season.*—Early, long and continuous flowering habit; plants begin flowering about six weeks after planting and continuously flower from spring to late autumn in California.

*Postproduction longevity.*—Flowers last about three to four days on the plant; flowers not persistent.

*Flower buds.*—Height: About 1.7 cm. Diameter: About 4 mm. Shape: Obovate; with slender tubular base. Color: Close to N187C to N187D.

*Flower diameter.*—About 2.4 cm.

*Flower depth.*—About 2.8 cm.

*Petals.*—Quantity per flower: Typically five in a single whorl; petals fused at the base. Lobe length: About 1.4 cm. Lobe width: About 1.4 cm. Tube length: About 1.3 cm. Tube diameter: About 1 mm. Shape: Roughly spatulate. Apex: Rounded. Margin: Entire. Texture, upper and lower surfaces: Smooth, glabrous; slightly rugose. Color: Developing petals, upper surface: Close to N87A. Developing petals, lower surface: Close to N88C. Fully expanded petals, upper surface: Close to 90C; towards the center, close to 12B; color becoming closer to N87D with development. Fully expanded petals, lower surface: Close to N88C to N88D; color becoming closer to 85C with development. Throat: Close to 157D. Tube: Close to 157D.

*Sepals.*—Quantity per flower: Typically five in a single whorl, fused at base; star-shaped calyx. Length: About 8 mm. Width: About 3 mm. Shape: Lanceolate. Apex: Acute. Margin: Entire. Texture, upper and lower surfaces: Pubescent. Color, upper and lower surfaces: Close to 147B.

*Peduncles.*—Length: About 1 cm. Diameter: About 1 mm. Aspect: About 45° from the lateral branch axis. Strength: Strong. Texture: Pubescent. Color: Close to 146B.

*Reproductive organs.*—Stamens: Quantity per flower: Typically five. Filament length: About 6 mm. Filament color: Close to 145D. Anther length: About 1.5 mm. Anther shape: Oval. Anther color: Close to 6C. Pollen amount: Moderate. Pollen color: Close to 6A. Pistils: Quantity per flower: One. Pistil length: About 2.5 cm. Stigma shape: Anvil-shaped. Stigma color: Close to 144C. Style length: About 2.1 cm. Style color: Close to 145D. Ovary color: Close to 189A.

*Seed/fruit.*—Seed and fruit development have not been observed.

Disease/pest resistance: Plants of the new *Nierembergia* have not been noted to be resistant to pathogens and pests common to *Nierembergia*.

Garden performance: Plants of the new *Nierembergia* have been observed to have good garden performance and tolerate rain, wind and temperatures from about −3° C. to about 43° C.

It is claimed:

1. A new and distinct *Nierembergia* plant named 'USNRB1201' as illustrated and described.

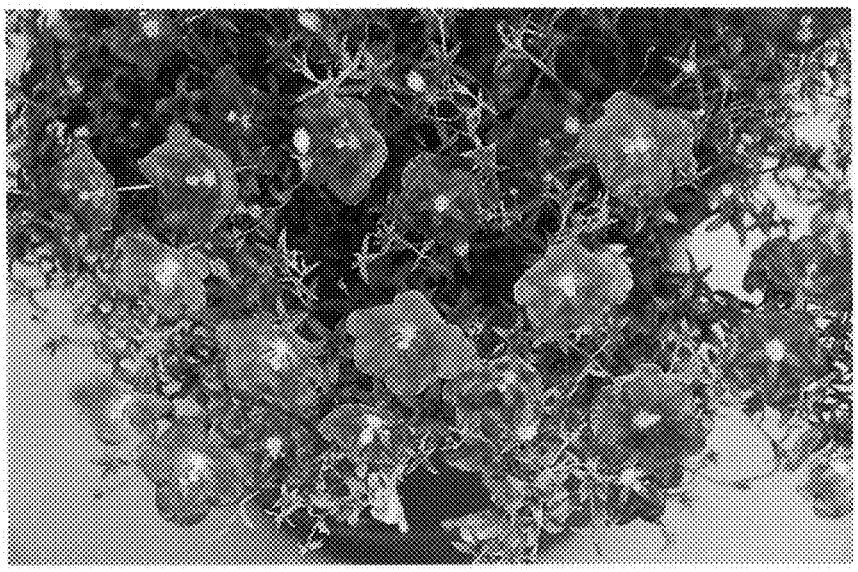
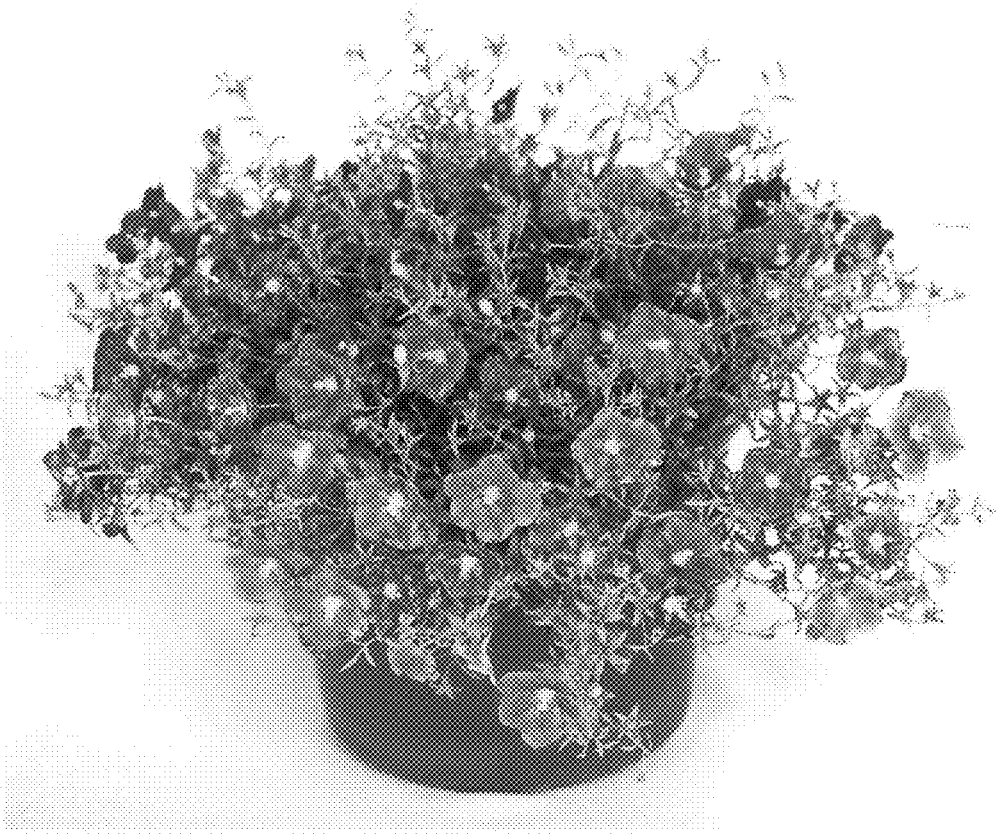

* * * * *